United States Patent [19]

Grabowski et al.

[11] Patent Number: 5,641,516
[45] Date of Patent: Jun. 24, 1997

[54] COMPOSITIONS WHICH CONTAIN ACTIVE SUBSTANCES AND ARE IN THE FORM OF SOLID PARTICLES

[75] Inventors: Sven Grabowski, Ludwigshafen; Axel Sanner, Frankenthal; Joerg Rosenberg, Ellerstadt, all of Germany

[73] Assignee: BASF Aktiengesellschaft, Ludwigshafen, Germany

[21] Appl. No.: 511,489

[22] Filed: Aug. 7, 1995

Related U.S. Application Data

[63] Continuation of Ser. No. 102,751, Aug. 6, 1993, abandoned.

[30] Foreign Application Priority Data

Aug. 13, 1992 [DE] Germany .................. 42 26 753.6

[51] Int. Cl.⁶ .................................................. A61K 9/14
[52] U.S. Cl. .................... 424/489; 424/497; 424/464; 424/494; 424/480; 424/488; 424/486
[58] Field of Search .................... 424/78, 468, 489, 424/480, 486

[56] References Cited

U.S. PATENT DOCUMENTS 3,432,592  3/1969  Speiser .................... 424/489
4,803,079  2/1989  Hsiao et al. .................... 424/468
4,814,168  3/1989  Sablotsky et al. .................... 424/78
5,273,760 12/1993  Oshlack et al. .................... 424/480

FOREIGN PATENT DOCUMENTS 440462  8/1991  European Pat. Off. .

*Primary Examiner*—Thurman K. Page
*Assistant Examiner*—William E. Benston, Jr.
*Attorney, Agent, or Firm*—Keil & Weinkauf

[57] ABSTRACT

Compositions which contain active substances and are in the form of solid particles can be obtained by intimately mixing the active substance with a water-soluble melt composed of a) 10–90% by weight of a water-soluble polymer A with a viscosity $V_a$ of 1,000–120,000 cps and b) 10–90% by weight of a water-soluble polymer B with a viscosity $V_b$ of 1–500 cps as carrier substance, where the viscosities $V_a$ and $V_b$ are those of a 2% by weight aqueous solution at 20° C., measured by the ASTM D 2363-72 capillary method (European Pharmacopoeia, Vol. III, p. 37), and processing the melt with shaping to give the particles.

7 Claims, No Drawings

COMPOSITIONS WHICH CONTAIN ACTIVE SUBSTANCES AND ARE IN THE FORM OF SOLID PARTICLES

This application is a continuation of application Ser. No. 08/102,751, filed on Aug. 6, 1993, now abandoned.

The present invention relates to compositions which contain active substances and are in the form of solid particles, obtainable by intimately mixing the active substance with a water-soluble melt composed of a) 10–90% by weight of a water-soluble polymer A with a viscosity $V_a$ of 1,000–120,000 cps and b) 10–90% by weight of a water-soluble polymer B with a viscosity $V_b$ of 1–500 cps as carrier substance, where the viscosities $V_a$ and $V_b$ are those of a 2% by weight aqueous solution at 20° C., measured by the ASTM D 2363-72 capillary method (European Pharmacopoeia, Vol. III, p. 37), and processing the melt with shaping to give the particles.

The present invention also relates to a process for producing these compositions and to the use thereof for purposes in human and veterinary medicine and in crop protection.

Compositions which contain active substances and are composed of water-soluble polymers as carrier substance with delayed release of active substance are generally known. The delayed release is normally achieved by sparingly soluble or insoluble additives such as copolymers of methyl methacrylate and acrylic acid as well as waxes and fats (U.S. Application Ser. No. 3,432,592).

EP-A 440 462 describes compositions which contain active substances and are in the form of compressed tablets and which contain mixtures of high-viscosity and low-viscosity hydroxypropylmethylcelluloses as carrier substances. The disadvantage of the formulations is that they are unsatisfactory in respect of release because the active substance is embedded as crystals in the polymeric carrier substance and cannot be completely absorbed after intake. In addition, an evenly delayed release is observed only with certain mixing ratios of high- to low-viscosity hydroxypropylmethylcellulose. In addition, the production of these formulations is industrially very costly because it requires a high pressure for compression and a plurality of screening steps for uniform particle sizes.

It is an object of the present invention to produce compositions which contain active substances and are in the form of solid particles and which have a delayed and uniform release of active substances as well as good absorption.

We have found that this object is achieved by the compositions defined at the outset.

The present invention also relates to a process for the production thereof, the presentations thereof and the use thereof for purposes in human and veterinary medicine and in crop protection in which delayed release of the active substances is required.

The compositions according to the invention contain as carrier substance a water-soluble melt composed of a) a water-soluble polymer A with a viscosity $V_a$ of 1,000–120,000 cps, preferably 3,500–120,000 cps and b) a water-soluble polymer B with a viscosity $V_b$ of 1–500 cps, preferably 1–100 cps, where the viscosities $V_a$ and $V_b$ are those of a 2% by weight aqueous solution at 20° C., measured by the ASTM D 363-72 capillary method (European Pharmacopoeia, Vol. III, p. 37).

The water-soluble melt is composed of a) 10–90% by weight, preferably 10–50% by weight, of a polymer A and b) 10–90% by weight, preferably 50–90% by weight, of a polymer B.

Suitable water-soluble polymers A with a viscosity $V_a$ are the following gel-forming substances:

alkylcelluloses such as methylcellulose hydroxyalkylcelluloses such as hydroxymethylcellulose, hydroxyethylcellulose, hydroxypropylcellulose and hydroxybutylcellulose hydroxyalkylalkylcelluloses such as hydroxyethylmethylcellulose and hydroxypropylmethylcellulose carboxyalkylcelluloses such as carboxymethylcellulose alkali metal salts of carboxyalkylcelluloses such as sodium carboxymethylcellulose carboxyalkylalkylcelluloses such as carboxymethylethylcellulose carboxyalkylcellulose esters starches pectins such as sodium carboxymethylamylopectin chitin derivatives such as chitosan polysaccharides such as alginic acid, its alkali metal and armonium salts, carrageenans, galactomannans, tragacanth, agar-agar, gumarabic, guar gum and xanthan gum polyacrylic acid and its salts polymethacrylic acid and its salts polyvinyl alcohol polyvinylpyrrolidone polyalkylene oxides such as polyethylene oxide and polypropylene oxide and copolymers of ethylene oxide and propylene oxide and mixtures of these substances.

Preferred polymers A are methylcellulose, hydroxypropylcellulose and hydroxypropylmethylcellulose, especially hydroxypropylmethylcellulose.

Examples of water-soluble polymers B with a viscosity $V_b$ are alkylcelluloses such as methylcellulose hydroxyalkylcelluloses such as hydroxymethylcellulose, hydroxyethylcellulose, hydroxypropylcellulose and hydroxybutylcellulose hydroxyalkylalkylcelluloses such as hydroxyethylmethylcellulose and hydroxypropylmethylcellulose polyvinyl alcohol polyvinylpyrrolidone polyvinyl acetate N-vinylpyrrolidone/vinyl acetate copolymers and mixtures thereof.

Preferred polymers B are hydroxypropylcellulose, polyvinylpyrrolidone and N-vinylpyrrolidone/vinyl acetate copolymers, especially hydroxypropylcellulose and copolymers of 40–70% by weight N-vinylpyrrolidone and 30–60% by weight vinyl acetate.

"Water-soluble" means that at least 0.5 g, preferably 2 g, of the polymer dissolves, with or without gel formation, in 100 g of water at 20° C.

Suitable active substances are, besides vitamins, for example the compounds listed in EP-A 240 904, those which are preferably suitable being the active substances which are mentioned as particularly preferred in the cited publication. The principle according to the invention is particularly suitable for compositions containing the cardiovascular agent nifedipine (dimethyl 1,4-di-hydro-2,6-dimethyl-4-(2-nitrophenyl)-3,5-pyridinedicarboxylate) as active substance.

The active substances also include those used as bioactive substances in the crop protection sector.

The compositions according to the invention can be produced either by melting the active substances directly as mixture with polymers A and B or by mixing them with the previously prepared polymer melt.

The particular active substance can be present in the compositions according to the invention in amorphous form, virtually homogeneously dispersed in the melt, which is advantageous for evenly delayed release and good absorption. The substances which are present as a molecular dispersion in a polymer melt are normally also called "solid solutions".

The compositions according to the invention can contain various concentrations of the active substances depending on the activity and rate of release. Thus, possible amounts of active substance per dose unit are from about 0.1 to 90% by weight—based on the melt—preferably from 0.5 to 60% by weight.

The active substance is mixed with the melt in a conventional way in extruders, preferably in single- and twin-screw extruders, at from 50° to 200° C. The shaping of the melts which contain the active substances to give the compositions according to the invention can take place, for example, by calendering the extrudate by the method described in EP-A 240 906, and by the process disclosed in DE-A 38 30 355, by comminuting the extrudate with rotating knives to give fragments which have a solidified surface but are still deformable and are of equal volume, and subsequently compressing to tablets in conventional tableting machines.

The mixing of the active substance with the melt can also take place in other apparatus which is suitable for this purpose and is conventionally used for processing plastics, e.g. calenders and injection molds.

The compositions according to the invention can also contain conventional pharmaceutical auxiliaries such as fillers, lubricants, mold release agents, flow regulators, plasticizers, colorants and stabilizers, in amounts of up to about 50% of the weight of the melt (=100%) which contains the active substance.

Examples of fillers are the oxides of magnesium, aluminum, silicon and titanium, and the amount of filler is preferably about 0.05–50% by weight.

Examples of lubricants and mold release agents are calcium, magnesium and aluminum stearates as well as talc and silicones, and the amount is preferably about 0.1–3% by weight.

Examples of flow regulators are the mono-, di- and triglycerides of long-chain fatty acids, waxes and lecithins, and the amount is preferably about 0.1–5% by weight.

Examples of plasticizers are, besides low molecular weight polyalkylene oxides such as polyethylene glycol, polypropylene glycol and polyethylene/propylene glycol, also polyhydric alcohols such as propylene glycol, glycerol, pentaerythritol and sorbitol, and sodium diethyl sulfosuccinate, mono-, di- and triacetates of glycerol and polyethylene glycol stearate. The amount of plasticizer is preferably about 0.5–15% by weight.

Examples of colorants are azo dyes, organic and inorganic pigments as well as natural coloring agents, and the amount is preferably about 0.5–3% by weight.

Examples of stabilizers are light stabilizers, antioxidants, free radical traps and stabilizers preventing microbial contamination, and the amount thereof is preferably about 0.01–0.05% by weight.

It is also possible for acidic additives to be present to control the solubility of the active substance. Conventional examples are citric acid and succinic acid.

It is possible either to mix the auxiliaries into the polymer melt which already contains the active substances, or to incorporate them mixed with the active substances into the polymer melt. It is furthermore possible for mixtures of auxiliaries, active substances and polymers A and B to be directly melted. The latter method is generally customary.

The compositions containing active substances according to the invention are used in the form of powders, granules, tablets and pellets for purposes in human and veterinary medicine and in crop protection where delayed release of the active substances is required.

To achieve additional delay of release of active substances, the compositions according to the invention can be covered with coating materials such as ethylcellulose, hydroxypropylcellulose, hydroxypropylmethylcellulose, cellulose acetate phthalate, polymethacrylates and shellac. It is advisable, especially for purposes in human medicine, to cover the compositions with colored coatings, e.g. composed of titanium dioxide and colored pigments, to improve the appearance. Coatings suitable for improving the taste are those composed of, for example, glucose, sucrose, xylitol and mannitol.

The novel compositions which contain active substances and are in the form of solid particles have advantages by comparison with those of the prior art in that they release the active substances, irrespective of the composition of substances, with uniform delay and good absorption without losing insoluble residues. The virtually homogeneous dispersion of the active substance in the polymeric carrier substance in the form of a solid solution is achieved by simple production methods without frequent screening steps and without high pressures for compression.

EXAMPLES 1 TO 7

The following commercially available polymers were used to produce compositions containing the active substances:

Polymer A:

A/1 Methylcellulose, $V_a$=8,000 cps (Metolose® SM 8000 from Shin-Etsu Chemical)

A/2 Hydroxypropylmethylcellulose, $V_a$=4,000 cps (Methocel® F4 M from Dow Chemical)

A/3 Hydroxypropylmethylcellulose, $V_a$=100,000 cps (Methocel® K100 M from Dow Chemical)

Polymer B:

B/1 Copolymer of 60% by weight N-vinylpyrrolidone (NVP) and 40% by weight vinyl acetate, $V_b$=5 cps (Kollidon® VA 64 from BASF AG)

B/2 Hydroxypropylmethylcellulose, $V_b$=100 cps (Methocel® K100 LV from Dow Chemical)

B/3 Hydroxypropylcellulose, $V_a$=2 cps (Klucel® EF from Hercules)

The following substances were used as auxiliaries C:

C/1 Polyethylene glycol stearate (PEG-9 stearate; macrogol stearate 400 complying with DAB 9) (Cremophore® S9 from BASF AG)

C/2 Polyethylene glycol, $M_w$=4,000 (Lutrol® E 4000 from BASF AG)

C/3 Polyethylene glycol, $M_w$=6,000 (Lutrol® E 6000 from BASF AG) ($M_w$=weight average molecular weight)

The amounts of polymers A and B indicated in the Table under Examples 1 to 7 were in some cases mixed with the auxiliaries C and were in each case mixed with the active substance nifedipine in the amounts specified therein. The complete mixture was produced in a twin-screw extruder and then extruded with the extruder barrel being heated through five temperature zones (60°, 80°, 100°, 120° and 130° C.). The polymer extrudate emerging from the extruder die at the various temperatures (130°–150° C.) was introduced into a calender with mutually opposing recesses in the roll surfaces and compression molded to 250 mg tablets.

The release of active substance was measured by the USP XXI paddle method. This in vitro test method is used to determine the rate of dissolution of moldings (e.g. tablets) containing active substances.

To do this, 900 ml of a phosphate buffer solution of pH 6.8 were equilibrated at 37° C. in a 1 l round-bottom vessel. During the test, the 250 mg tablet was located in the center of the round bottom of the vessel below the paddle which was rotated at 100 rpm. The test lasted 8 hours in each case, after which the amount of released active substance was determined by UV spectroscopy. The release of active substance was found to be proportional to time in all cases.

The details of these tests and their results are to be found in the Table.

TABLE

| Example | Polymer A (% by weight) | | Polymer B (% by weight) | | Auxiliary C (% by weight) | | Nifedipine (% by weight) | Temperature of the die (°C.) | Release of active substance after 8 h (%) |
|---|---|---|---|---|---|---|---|---|---|
| 1 | 50 | A/1 | 50 | B/1 | — | | 25 | 140 | 64 |
| 2 | 50 | A/2 | 50 | B/1 | — | | 25 | 130 | 59 |
| 3 | 75 | A/2 | 25 | B/1 | — | | 25 | 150 | 27 |
| 4 | 37.5 | A/3 | 62.5 | B/1 | — | | 25 | 140 | 36 |
| 5 | 10 | A/1 | 50 | B/2 | — | | 25 | 130 | 66 |
|   |    |     | 40 | B/3 |   |   |    |     |    |
| 6 | 10.5 | A/2 | 39.5 | B/2 | 1.3 | C/1 | 26.3 | 130 | 56 |
|   |      |     | 50 | B/3 | 3.9 | C/2 |      |     |    |
| 7 | 73.4 | A/2 | 26.6 | B/3 | 6.6 | C/3 | 26.6 | 140 | 54 |

We claim:

1. A solid composition comprising an active substance, said composition obtained by a process comprising, blending the active substance with a polymeric melt, said polymeric melt comprising a) 10–90% by weight of a water-soluble polymer A with a viscosity $v_a$ of 1,000–120,000 cps and b) 10–90% by weight of a water-soluble polymer B with a viscosity $v_b$ of 1–500 cps where the viscosities $v_a$ and $v_b$ are those of a 2% by weight aqueous solution at 20° C., measured by the ASTM D 2363-72 capillary method (European Pharmacopeia, Vol. III, p. 37), until the active substance is homogeneously dispersed in the polymeric melt; and then shaping the polymeric melt.

2. The composition defined in claim 1, wherein the polymeric melt comprises a) a water-soluble polymer A with a viscosity $V_a$ of 3,500–120,000 cps and b) a water-soluble polymer B with a viscosity $V_b$ of 1–100 cps.

3. The composition defined in claim 1, wherein the polymeric melt comprises a) 10–50% by weight of a water-soluble polymer A and b) 50–90% by weight of a water-soluble polymer B.

4. The composition defined in claim 1, wherein the polymeric melt comprises methylcellulose, hydroxypropylcellulose and/or hydroxypropylmethylcellulose as polymer A.

5. The composition defined in claim 1, wherein the polymeric melt comprises hydroxypropylcellulose, polyvinylpyrrolidone and/or N-vinylpyrro-lidone/vinyl acetate copolymers as polymer B.

6. The composition defined in claim 1, wherein the active substance is nifedipine.

7. A process for producing the composition defined in claim 1, which comprises mixing the active substance with a water-soluble melt of polymers A and B, and processing the melt with shaping to give the particles.

* * * * *